US006277631B1

(12) United States Patent
Noah et al.

(10) Patent No.: US 6,277,631 B1
(45) Date of Patent: Aug. 21, 2001

(54) RECOMBINANT PROTEINS WITH THE IMMUNOREACTIVITY OF HEPATITIS B VIRUS E ANTIGEN (HBEAG), A PROCESS FOR THE PREPARATION THEREOF AND THE USE THEREOF IN IMMUNOASSAYS AND VACCINES

(75) Inventors: Michael Noah; Michael Bröker, both of Marburg (DE)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 08/445,585

(22) Filed: May 22, 1995

Related U.S. Application Data

(63) Continuation of application No. 08/197,537, filed on Feb. 17, 1994, now abandoned, which is a continuation of application No. 07/846,194, filed on Mar. 6, 1992, now abandoned.

(30) Foreign Application Priority Data

Mar. 9, 1991 (DE) ................................. 41 07 612

(51) Int. Cl.[7] .............................. C12Q 1/70; A61K 39/29
(52) U.S. Cl. .................... 435/320.1; 435/69.1; 435/69.3; 435/69.8; 435/69.9; 435/471; 435/476; 435/483; 435/940; 536/23.1; 536/23.72; 530/826
(58) Field of Search ................................. 435/69.3, 69.8, 435/69.9, 320.1, 69.1, 476, 471, 483, 940; 536/23.72, 23.1; 530/826

(56) References Cited

U.S. PATENT DOCUMENTS 5,082,783 * 1/1992 Ernst et al. .

FOREIGN PATENT DOCUMENTS

| 0 075 395 | 3/1983 | (EP) . |
| 0 374 869 | 6/1990 | (EP) . |
| 2 635 115 | 2/1990 | (FR) . |
| WO 90/08960 | 8/1990 | (WO) . |
| WO 92/11368 | 7/1992 | (WO) . |

OTHER PUBLICATIONS

Kim et al., "Synthesis and Secretion of Hepatitis B e Antigen in Yeast", In Symposium on Viral Hepatitis and Liver Disease, 1160–1164, 1990.*
Sambrook et al., "Molecular Cloining a Laboratory Manual," Cold Spring Harbor Press, NY, 1989, 11.7–11.8.*
Bruss et al., Virology 163, 268–275, Feb. 1988.*
Sleep et al., Biotechnology, vol. 8, Jan. 1990, 42–46.*
Kingsman et al., Biotechnology & Genetic Engineering, Reviews, vol. 13, Sep. 1985, 377–416.*
Kim et al. "b", 1990 Symposium on Viral Hepatitus and Liver Disease, pp 1160–1164.*

Sambrook et al, "Moleculer Cloning a Labortory Manual" Cold Spring Harbor Press, NY, 1989. pp. 11.7–11.8.*
Pouwels et al., "Cloning Vectors a Labortory Manual" 1985 Elsevier, New York, pp VI–A–ii–1.*
Ammerer, Method in Enzymology, vol 101, Academic Press, NY. 1983, pp 192–201.*
Garcia et al., J. Cell Biol. 106, Apr. 1988. pp 1013–1104.*
Jean–Jean et al, Virology 17 , 1989. pp 99–106.*
Takehashi et al, J. of Immunol. 130(6) 1983. pp 2903–2907.*
Miyanahara et al, J. Virology 59. Jul., 1986, p 176–180.*
Seitfeld et al, J. Virology vol 63(2) Feb. 1989. p 798–808.*
Bruss et al., Virology 163, p 268–275, 1988.*
Broker, Biotechniques 5(6), 1987. p 516–518.*
Baldor et al, EMBO J. 6(1) 1987. pp 224–234.*
McLachlen et al, J. Virology 61(3) 1987. pp 684–692.*
Junker et al, NAR 24. 1987. pp 10117–10131.*
Mimms et a., Viral hepatitis and Liver disease, 1988, p 248–251.*
Sleep et al, Biotechnology vol 8, Jun. 199Opp 42–46.*
Kingsman et al, Biotechnology & Genetic Eng. Reviews vol 3, Sep. 1985 pp 377–416.*
Kim et al abstract, 1990 Symposium on viral Hepatitis & liver disease, Apr. 4–8, 1990, Houston Texas.*
Tong et al, Virology, 176. pp 596–603. 1990.*
Kim et al., "Synthesis and Secretion of Hepatitis B e Antigen in Yeast", 1990 Symposium on Viral Hepatitis and Liver Disease, pp. 1160–1164, Apr. 4–8, 1990, Houston, Texas.
Demonstration of Hepatitis B e Antigen in the Core of Dane Particles, K. Takahashi et al., Journal Ff Immunology, vol. 122, Jan. 1979, p. 275–279.
Production, Purification, and Immunological Characterization of a Recombinant DNA–Derived Hepatitis B e Antigen, L. Mimms et al, Viral Hepatitis and Liver Disease, p. 57.
Nucleotide Sequence Of The Hepatitis B Virus Genome (Subtype AYW) Cloned In *E. coli*, Francis Galibert et al., Nature, vol. 281, p. 646–650.
Molecular Cloning, A Laboratory Manual, Second Edition, Sambrook, Fritsch, and Maniatis.
New Expression Vectors for The Fission Yeast *Schizosaccharomyces Pombe* Michael Broeker et al., FEBS Letters 07145, vol. 248, No. 1,2, p. 105–110, May 1989.

(List continued on next page.)

Primary Examiner—Marianne P. Allen
Assistant Examiner—Mary K Zeman
(74) Attorney, Agent, or Firm—Finnegan, Henderson, Farabow, Garrett and Dunner, L.L.P.

(57) ABSTRACT

Recombinant yeast expression vectors with the features indicated in the patent claims are described. These recombinant yeast expression vectors can be used for the preparation of HBeAg in yeast host organisms. Appropriate expression systems, transformed host organisms, diagnostic aids and medicinal agents are additionally described.

12 Claims, 3 Drawing Sheets

OTHER PUBLICATIONS

Figure 1:
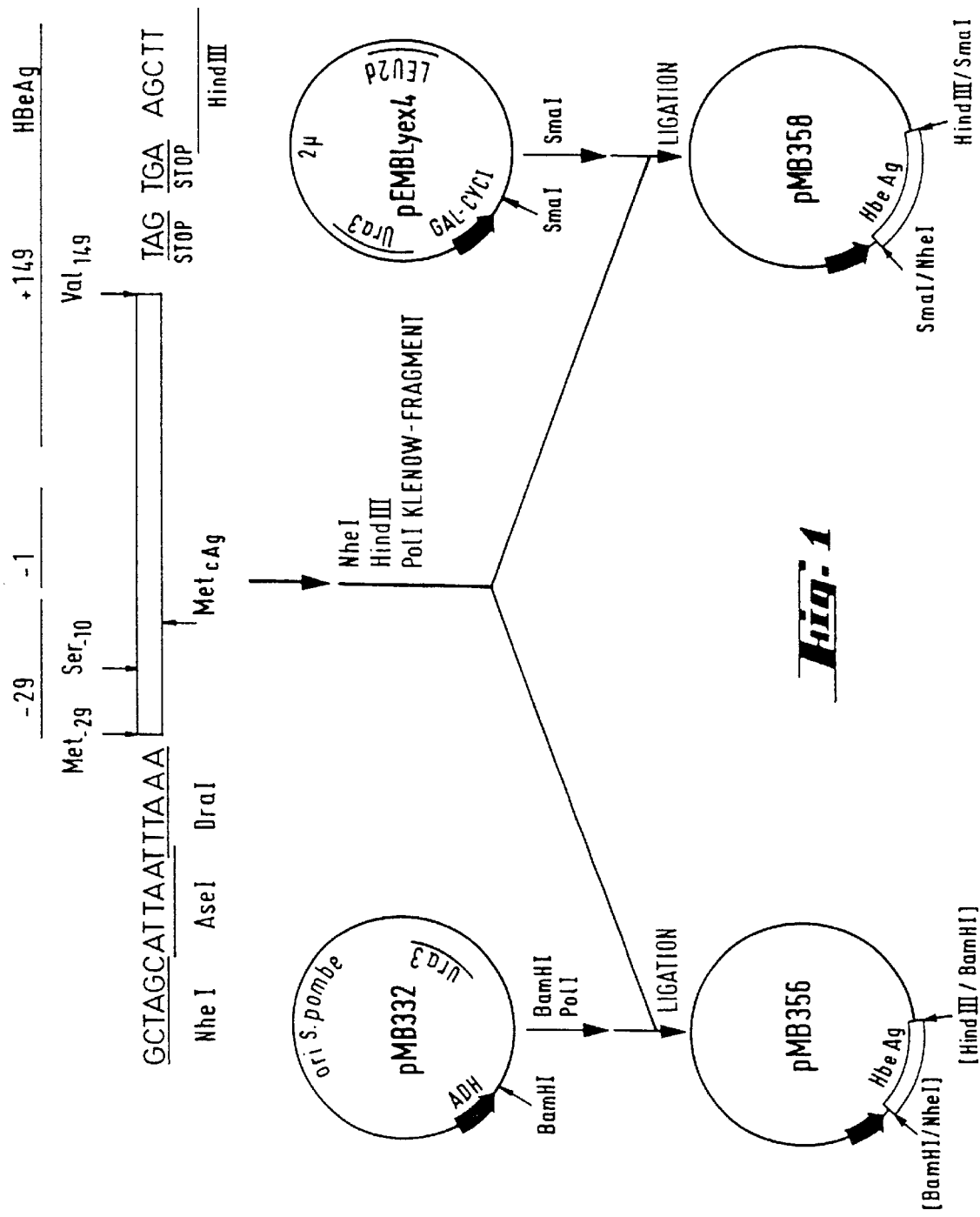

Plasmid Vectors Carrying The Replication Origin Of Filamentous Single–Stranded Phages, Cesareni et al., Genetic Engineering, vol. 9 p. 135–154.

Transformation Of Intact *Schizosaccharomyces Pombe* Cells With Plasmid DNA, Michael Broeker, BioTechniques, vol. 5, No. 6 (1987), p. 516–158.

A Novel Leader Peptide Which Allows Efficient Secretion Of A Fragment Of Human Interleukin 1β in *Saccharomyces Cerevisiae*, C. Baldari et al The EMBO Journal, vol. 6, No. 1, p. 229–234 (1987).

Anti–HBc–Bestimmung Mittels Monoklonaler Antikoerper, Michael Noah et al., BioEngineering 2/88, p. 22–30. No Translation.

Antigenic Determinants And Functional Domains In Core Antigen and E Antigen From Hepatitis B Virus, J. Salfeld et al., Journal Of Virology Feb. 1989, vol. 63, No. 2, p. 798–808.

Demonstration Of Two Distinct Antigenic Determinants On Hepatitis B e Antigen By Monoclonal Antibodies, M. Imai et al., The Journal Of Immmunology, vol. 128, No. 1, Jan. 1982. p. 69–72.

Monoclonal Antibodies To Hepatitis Be Antigen (HBeAg) Derived From Hepatitis B Core Antigen (HBcAg): Their Use In Characterization And Detection Of HBeAg, R. Bridget Ferns et al., J. Gen. Virol. (1984) 65, p. 899–908.

Miyanohara et al., Journal of Virology, vol. 59, No. 1, (Jul. 1986). pp. 176–180.

McLachlan et al., Journal of Virology, vol. 61, No. 3, (Mar. 1987) pp. 683–692.

Junker et al., Nucleic Acids Research, vol. 15, No. 24, (Dec. 1987) pp. 10117–10132.

English Abstract of FR 2635115.

* cited by examiner

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 5 amino acids
      (B) TYPE: amino acid
      (D) TOPOLOGY: linear (ii) MOLECULE TYPE: peptide (xi) SEQUENCE DESCRIPTION: SEQ ID NO:1:

Thr Arg Val Lys Arg (2) INFORMATION FOR SEQ ID NO:2:

(i) SEQUENCE CHARACTERISTICS:
        (A) LENGTH: 477 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..477

(xi) SEQUENCE DESCRIPTION: SEQ ID NO:2:

```
TCC AAG CTG TGC CTT GGG TGG CTT TGG GGC ATG GAT ATC GAT CCT TAT      48
Ser Lys Leu Cys Leu Gly Trp Leu Trp Gly Met Asp Ile Asp Pro Tyr
-10          -5                   1               5

AAA GAA TTC GGA GCT ACT GTG GAG TTA CTC TCG TTT CTC CCG AGT GAC      96
Lys Glu Phe Gly Ala Thr Val Glu Leu Leu Ser Phe Leu Pro Ser Asp
             10                  15                  20

TTC TTT CCT TCA GTA CGA GAT CTT CTG GAT ACC GCC AGC GCG CTG TAT     144
Phe Phe Pro Ser Val Arg Asp Leu Leu Asp Thr Ala Ser Ala Leu Tyr
         25                  30                  35

CGG GAA GCC TTG GAG TCT CCT GAG CAC TGC AGC CCT CAC CAT ACT GCC     192
Arg Glu Ala Leu Glu Ser Pro Glu His Cys Ser Pro His His Thr Ala
     40                  45                  50

CTC AGG CAA GCA ATT CTT TGC TCG GGG GAG CTC ATG ACT CTG GCC ACG     240
Leu Arg Gln Ala Ile Leu Cys Ser Gly Glu Leu Met Thr Leu Ala Thr
 55                  60                  65                  70

TGG GTG GGT GTT AAC TTG GAG GAT CCT GCT TCT AGA GAC CTG GTA GTC     288
Trp Val Gly Val Asn Leu Glu Asp Pro Ala Ser Arg Asp Leu Val Val
                 75                  80                  85

AGT TAT GTC AAC ACT AAT ATG GGT TTA AAG TTC AGG CAA CTC TTG TGG     336
Ser Tyr Val Asn Thr Asn Met Gly Leu Lys Phe Arg Gln Leu Leu Trp
             90                  95                 100

TTT CAC ATT AGC TGC CTC ACT TTC GGC CGA GAA ACA GTT ATA GAA TAT     384
Phe His Ile Ser Cys Leu Thr Phe Gly Arg Glu Thr Val Ile Glu Tyr
        105                 110                 115

TTG GTG TCT TTC GGA GTG TGG ATC AGA ACT CCT CCA GCT TAT AGG CCT     432
Leu Val Ser Phe Gly Val Trp Ile Arg Thr Pro Pro Ala Tyr Arg Pro
    120                 125                 130

CCG AAT GCC CCT ATC CTG TCG ACA CTC CCG GAG ACT ACT GTT GTT         477
Pro Asn Ala Pro Ile Leu Ser Thr Leu Pro Glu Thr Thr Val Val
135                 140                 145
```

(2) INFORMATION FOR SEQ ID NO:3:

(i) SEQUENCE CHARACTERISTICS:
        (A) LENGTH: 159 amino acids
        (B) TYPE: amino acid
        (D) TOPOLOGY: linear (ii) MOLECULE TYPE: protein (xi) SEQUENCE DESCRIPTION: SEQ ID NO:3:

```
Ser Lys Leu Cys Leu Gly Trp Leu Trp Gly Met Asp Ile Asp Pro Tyr
-10          -5                   1               5

Lys Glu Phe Gly Ala Thr Val Glu Leu Leu Ser Phe Leu Pro Ser Asp
             10                  15                  20

Phe Phe Pro Ser Val Arg Asp Leu Leu Asp Thr Ala Ser Ala Leu Tyr
         25                  30                  35
```

```
Arg Glu Ala Leu Glu Ser Pro Glu His Cys Ser Pro His His Thr Ala
    40                  45                  50

Leu Arg Gln Ala Ile Leu Cys Trp Gly Glu Leu Met Thr Leu Ala Thr
55                  60                  65                  70

Trp Val Gly Val Asn Leu Glu Asp Pro Ala Ser Arg Asp Leu Val Val
                75                  80                  85

Ser Tyr Val Asn Thr Asn Met Gly Leu Lys Phe Arg Gln Leu Leu Trp
                90                  95                  100

Phe His Ile Ser Cys Leu Thr Phe Gly Arg Glu Thr Val Ile Glu Tyr
            105                 110                 115

Leu Val Ser Phe Gly Val Trp Ile Arg Thr Pro Pro Ala Tyr Arg Pro
        120                 125                 130

Pro Asn Ala Pro Ile Leu Ser Thr Leu Pro Glu Thr Thr Val Val
135                 140                 145
```

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GCTAGCATTA ATTTAAA                                       17

(2) INFORMATION FOR SEQ ID NO:5:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

TAGTGAAGCT T                                             11

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GCTAGCATTA ATTTAAAATG                                   20

(2) INFORMATION FOR SEQ ID NO:7:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TAGTGAAGCT TCCGGGCCGG CGATAATACG CCGGCCCGTT TTTTTTCAGC TGCATTAAT    59

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GCTAGCCCGG GTCAAAAGA                                                19

(2) INFORMATION FOR SEQ ID NO:9:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

TGATGAAGCT T                                                        11

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CAAGGTACCC GGGTCAAAAG ATCC                                          24

(2) INFORMATION FOR SEQ ID NO:11:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:11:

Met Asn Ile Phe Tyr Ile Phe Leu Phe Leu Leu Ser Phe Val Gln Gly
1               5                   10                  15

(2) INFORMATION FOR SEQ ID NO:12:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:12:

-continued

```
Met Gln Leu Phe His Leu Cys Leu Ile Ile Ser Cys Ser Cys Pro Thr
            -25                 -20                 -15

Val Gln Ala
```

RECOMBINANT PROTEINS WITH THE IMMUNOREACTIVITY OF HEPATITIS B VIRUS E ANTIGEN (HBEAG), A PROCESS FOR THE PREPARATION THEREOF AND THE USE THEREOF IN IMMUNOASSAYS AND VACCINES

This application is a continuation of application Ser. No. 08/197,537 filed Feb. 17, 1994 abandoned, which is a continuation of originally filed application Ser. No. 07/846,194 filed Mar. 6, 1992, now abandoned.

The invention relates to recombinant proteins with the immunoreactivity of hepatitis B virus e antigen (HBeAg), to a process for the preparation thereof in yeasts and to the use thereof in immunoassays and in vaccines.

Immunoassays nowadays play an important part in the diagnosis of hepatitis B virus (HBV) infection. Thus, the acute phase of an infection is characterized by immunological detection of hepatitis B virus surface antigen (HBsAg). Determination of other HBV parameters allows confirmation of the diagnosis or differential diagnosis. Thus, it is assumed that HBsAg- and HBeAg-positive samples are acutely infectious, whereas the appearance of antibodies against HBeAg (anti-HBeAg-antibodies) marks the start of the period of patient convalescence.

Radioimmunoassays and enzyme-linked immunoassays have become used world-wide for determining HBeAg and anti-HBeAg-antibodies and have substantially displaced other less sensitive techniques such as agglutination methods. These assays operate on the "sandwich principle". A solid phase, for example the wells of a microtiter plate or beads which are coated with human or mouse anti-HBeAg antibodies, is incubated with the patient's sample. If the sample contains HBeAg, it binds to the solid-phase antibodies. Unbound constituents are removed in a washing step. The HBeAg bound to the solid phase is labeled during a second incubation with an anti-HBeAg antibody which is coupled to an enzyme or radioisotope. After another washing step, detection is carried out by the conversion of a substrate or by measuring the radio-activity of this ternary complex.

The same reagents and the same assay scheme can be used to detect anti-HBeAg-antibodies when a defined amount of HBeAg (the so-called neutralization reaction) is also added to the sample. If the test material, usually a serum sample, contains no anti-HBeAg-antibodies, a certain signal is generated thereby. However, if anti-HBeAg antibodies are present in the sample, they bind to the HBeAg of the neutralization reagent and prevent its binding to the solid phase and thus also the formation of the signal. This type of assay design thus combines aspects of the sandwich and of the competitive assay principle.

Assay systems for determining HBeAg and anti-HBeAg-antibodies in accordance with the principles described above can be obtained from several manufacturers and are also described many times in the literature (for example Abbott HBe(rDNA), Wiesbaden; Behring $^R$Enzygnost-HBe, Marburg; Sorin Biomedica EBK EIA, Düsseldorf).

To check that the assay is carried out correctly, all assay systems for determining HBeAg use a so-called positive control which contains a defined amount of HBeAg and thus must give rise to a defined signal if the assay has been carried out correctly. If this signal is not reached, the assay run is worthless because of the obvious error in carrying it out, and it must be repeated. For determination of anti-HBeAg antibodies, in fact HBeAg is in principle necessary in the neutralization reagent, as explained above, for carrying out the assay.

Some of the assay systems established to date use HBeAg which has had to be obtained from the blood of HBV-infected people, because it has not been possible to establish cell culture systems for growing the virus. The disadvantage of this material is the difficulty of obtaining large quantities of high-titer HBeAg-positive serum from the infected people.

In addition, manipulation of HBeAg-positive serum is, because of its infectious risk, possible only with elaborate and costly safety precautions.

Currently, the only protection from hepatitis B infection is, besides general hygienic measures, regarded as being vaccination.

The only immunogen used in vaccines currently commercially available is HBsAg, although there have been indications for some years in the literature that it might be possible to achieve or improve vaccination protection by using HBcAg and/or HBeAg components, singly, as mixture or as fusion with another immunogen. It would therefore likewise be important for immunization purposes to generate by genetic engineering methods an HBeAg which has no infectious potential and which additionally ought to have advantages, compared with the materials known to date, owing to optimal immunoreactivity without further denaturation measures, and should be possible to prepare in sufficient quantities straightforwardly and at low cost.

The first papers which showed that denaturation of HBcAg of human origin in, for example, SDS causes it to lose a large part of the HBc immunoreactivity and instead gain HBe immunoreactivity appeared in 1979 and 1980 (for example Takahashi et al., J. Immunol. 122 (1979), 275–279). However, application of this method to HBcAg of human origin has no advantages over HBeAg of human origin because the problems of acquisition and infectiosity remain.

Once it became possible to express HBcAg by genetic engineering methods in E. coli, the denaturation technique was also carried out with rHBcAg. The disadvantage in this case too is that there is still a certain HBcAG immunoreactivity remaining in these preparations.

EP-A 075 395 then described a truncated recombinant HBcAg (up to amino acid 144) from E. coli, which had HBeAg immunoreactivity in addition to HBcAg immunoreactivity. However, it was again necessary to eliminate the remaining HBcAg immunoreactivity by denaturation measures.

Once Takahashi et al. (loc. cit.) were able to show that the C-terminal amino-acid sequence of HBeAg corresponds to HBcAg apart from amino acids being missing from position 150 onward, the truncated HBcAg was also expressed as fusion protein in E. coli. Even with this material it was necessary to eliminate the remaining HBcAg immunoreactivity by denaturation (Mimms et al., Vir. Hepatitis and Liver Disease (1988), 248–251).

Thus, in the early 1980s it was assumed that HBeAg represented a denaturation product and/or a breakdown product of HBcAg. However, it has emerged that a DNA sequence with an open reading frame of 29 amino acids is located in front of the translation start signal of HBcAg (pre C sequence, amino acids −29 to −1).

It is assumed on the basis of current knowledge that in the region of the HBcAg gene (pre C plus C sequence) two different mRNAs are read or one mRNA species codes for two different translation products. HBcAg-specific mRNA contains an open reading frame with codons +1 to +183, and translation results in HBcAg which comprises amino acids +1 to +183.

By contrast, HBeAg-specific mRNA contains an open reading frame with codons −29 to +183. Translation results in formation of a precursor molecule which contains amino acids −29 to +183. The first 19 amino acids of this precursor protein function as signal sequence and lead to translocation of the precursor protein into the endoplasmic reticulum (ER). During further processing there is also proteolytic elimination of the C-terminal amino acids from position 150 onward so that, finally, HBeAg is secreted into the bloodstream.

Despite being substantially identical in amino-acid sequence, HBcAg and HBeAg have completely different immunological, structural and functional properties. Since, moreover, transcription starts at different starting points and leads to different mRNAs, it must be assumed that HBcAg and HBeAg are, ultimately, encoded by different genes, although with a certain overlap.

The paper by Kim et al. (The 1990 International Symposium on Viral Hepatitis and Liver Disease, Houston, Tex., Apr. 4–8, 1990, poster abstract No. 62) may be mentioned here as an example of the importance of the signal sequence for the formation of HBeAg. It shows that only HBcAg-reactive material is obtained in the cytosol of yeasts when the intention is to express HBeAg without the signal sequence directly in yeasts, and describes that the HBeAg must be fused to the alpha-factor signal sequence if the intention is to obtain material which has predominantly HBeAg reactivity.

Secretion by means of the signal sequence of the alpha-factor has the disadvantages that this signal sequence is not cleaved or is wrongly cleaved in the host organism, or may lead to degradation of the secreted protein, and these events usually occur side by side. For example, the secretion of human albumin takes place less well due to the signal sequence of alpha-factor than with the protein-intrinsic signal sequence of albumin or with a signal sequence which is hybrid between K. lactis killer toxin and alpha-factor (Sleep et al., Bio/Technology (1990), 8, 42–46).

By contrast, it has been found that the expression of HBeAg without HBc reactivity takes place even without a signal sequence, that is to say results in HBeAg without HBcAg reactivity and without a foreign protein content. It has further been found that secretion or expression by means of the HBeAg-intrinsic signal sequence is brought about, which possibly results in an HBeAg which may comprise additional regions up to position −29 and thus may contain additional pre-C epitopes.

The object according to the invention is to mimic the process assumed to take place in the infected liver cell in order to obtain a recombinant protein with the greatest possible similarity or identity to the HBeAg of the human system—and thus optimal immunoreactivity.

The expression system therefore used according to the invention is the eukaryotic yeast system because it, in contrast to the E. coli system, has more complex post-translational modification mechanisms and thus has considerably greater similarity to the eukaryotic human system. On the other hand, the expression of heterologous genes in yeasts is, by comparison with human or other mammalian cell systems, easier to manipulate and less costly.

Yeast expression systems are described in a general form in Kingsman et al. (1985), "Heterologous gene expression in Saccharomyces cerevisiae", in: Biotechnology and Genetic Engineering Reviews, Vol. 3, pp. 377–416.

Thus the invention relates to recombinant yeast expression vectors which have the following features:

(a) a DNA sequence which is replicable in yeast;

(b) a yeast promoter;

(c) a DNA sequence which encodes a protein with the immunoreactivity of HBeAg;

(d) a transcription stop signal; and (e) a DNA sequence which encodes a yeast selection marker.

The term "DNA sequence which is replicable in yeast" indicates a yeast origin of replication on the basis of which the recombinant yeast expression vectors according to the invention can be multiplied in yeast cells and thus can be maintained. The term "protein with the immunoreactivity of HBeAg" relates both to complete HBeAg and to derivatives thereof which may have, by comparison with complete HBeAg, additions, insertions or deletions of amino acids.

The person skilled in the art is able to assay such derivatives of HBeAg for their immunoreactivity in simple preliminary tests in a customary manner as described hereinafter.

Furthermore, imunoreactive epitopes of HBeAg can be identified using customary computer programs.

The DNA sequence (c) comprises a DNA sequence coding for a protein with the immunoreactivity of HBeAg. The start is preferably located at the codon for amino acid −29 or −10 or +1. It is particularly preferred for the start to be located at one of the abovementioned codons and the end to be located at the codon for amino acid 149.

The term "transcription stop signal" indicates a DNA sequence which follows the DNA sequence encoding a protein with the immunoreactivity of HBeAg and ensures suitable termination of the process of transcription of this coding DNA sequence. The term "DNA sequence which encodes a yeast selection marker" relates to DNA sequences on the basis of which yeasts which contain a recombinant yeast expression vector according to the invention can be distinguished from the corresponding plasmid-free yeasts. Selection markers of this type for yeast are normally, for example, genes which complement genetic defects in the host cell.

In a preferred embodiment, the recombinant yeast expression vector according to the invention is a shuttle vector which is able to multiply not only in yeast host cells but also in bacterial host cells and thus can be maintained. This facilitates the construction of the recombinant yeast expression vectors according to the invention, because intermediate steps can be carried out in bacterial host organisms, which are easy to manipulate, for the cloning. These recombinant yeast expression vectors according to the invention thus have the following additional features:

(f) an origin of replication for bacteria; and (g) a DNA sequence which encodes a bacterial selection marker.

Shuttle vectors which are preferred according to the invention can be replicated in E. coli.

In another embodiment, the DNA sequence (c) which is present in the yeast expression vectors according to the invention encodes amino acids Ser −10 to Val +149 of HBeAg, as well as, at the N-terminus of this amino-acid sequence, the signal peptide of the killer toxin of Kluyveromyces lactis or a biologically active part of this signal peptide. The above mentioned signal peptide does not have the disadvantages associated with the signal peptide of alpha-factor. A modified signal sequence of K. lactis killer toxin is used as preferred embodiment, wherein the last 13 carboxy-terminal amino acids of the pre-pro sequence have been replaced by the following 5 amino acids Thr-Arg-Val-Lys-Arg (SEQ ID No:1). The dipeptide Lys-Arg functions in the signal sequence both of killer toxin and of alpha-factor as proteolytic cleavage site so that the newly produced hybrid signal sequence has two presumptive protease recognition sites.

The expression vectors mentioned in the examples contain HBeAg-specific DNA sequences of the strain ayw, as have been described by Galibert et al. in Nature 281 (1979), 646–650, although the intention is to embrace also the Preferred according to the invention is a DNA sequence (c) (SEQ ID NO:2) which encodes the amino-acid sequence (SEQ ID NO:3), indicated in the table, from Ser −10 to Val +149 of HBeAg:

| −10 | | | | | | | | | |
|---|---|---|---|---|---|---|---|---|---|
| TCC | AAG | CTG | TGC | CTT | GGG | TGG | CTT | TGG | GGC |
| ser | lys | leu | cys | leu | gly | trp | leu | trp | gly |
| ATG | GAt | ATC | GAt | CCT | TAT | AAA | GAA | TTC | GGA | GCT |
| met | asp | ile | asp | pro | tyr | lys | glu | phe | gly | ala |
| | ACT | GTG | GAG | TTA | CTC | TCG | TTT | cTc | CCg | agT |
| | thr | val | glu | leu | leu | ser | phe | leu | pro | ser |
| | GAC | TTC | TTT | CCT | TCA | GTA | CGA | GAT | CTT | CTg |
| | asp | phe | phe | pro | ser | val | arg | asp | leu | leu |
| | GAT | ACC | GCC | agc | GCg | CTG | TAT | CGG | GAA | GCC |
| | asp | thr | ala | ser | ala | leu | tyr | arg | glu | ala |
| | TTg | GAG | TCT | CCT | GAG | CAc | TGc | agc | CCT | CAC |
| | leu | glu | ser | pro | glu | his | cys | ser | pro | his |
| | CAT | ACT | GCc | CTC | AGG | CAA | GCA | ATT | CTT | TGC |
| | his | thr | ala | leu | arg | gln | ala | ile | leu | cys |
| | TCG | GGG | GAg | CTc | ATG | ACT | CTg | GCc | ACg | TGG |
| | trp | gly | glu | leu | met | thr | leu | ala | thr | trp |
| | GTG | GGT | GTT | AAc | TTG | GAG | GAT | CCT | GCt | TCT |
| | val | gly | val | asn | leu | glu | asp | pro | ala | ser |
| | AGA | GAC | CTg | GTA | GTC | AGT | TAT | GTC | AAC | ACT |
| | arg | asp | leu | val | val | ser | tyr | val | asn | thr |
| | AAT | ATG | GGt | tTA | AAG | TTC | AGG | CAA | CTC | TTG |
| | asn | met | gly | leu | lys | phe | arg | gln | leu | leu |
| | TGG | TTT | CAC | ATT | agc | TGc | CTC | ACT | TTc | GGc |
| | trp | phe | his | ile | ser | cys | leu | thr | phe | gly |
| | cGA | GAA | ACA | GTT | ATA | GAa | TAT | TTG | GTG | TCT |
| | arg | glu | thr | val | ile | glu | tyr | leu | val | ser |
| | TTC | GGA | GTG | TGG | ATc | AGA | ACT | CCT | CCA | GCT |
| | phe | gly | val | trp | ile | arg | thr | pro | pro | ala |
| | TAT | AGg | CCt | CCg | AAT | GCC | CCT | ATC | CTg | TCg |
| | tyr | arg | pro | pro | asn | ala | pro | ile | leu | ser |
| | ACA | CTc | CCG | GAG | ACT | ACT | GTT | Gtt | | |
| | thr | leu | pro | glu | thr | thr | val | val | | |
| | | | | | | | | +149 | | |

The DNA sequence indicated in the preceding table is particularly preferred according to the invention.

In another embodiment which is particularly preferred according to the invention, the signal peptide of killer toxin of Kluyveromyces lactis has the following amino-acid sequence:
Met-Asn-Ile-Phe-Tyr-Ile-Phe-Leu-Phe-Leu-Leu-Ser-Phe-Val-Gln-Gly (SEQ ID NO:11)

In another embodiment according to the invention of the recombinant yeast expression vector, DNA sequence (c') is a DNA sequence which hybridizes with one of the DNA sequences (c) indicated above encoding a protein with the immunoreactivity of HBeAg. In this connection, the term "to hybridize" preferably means a hybridization under hybridization conditions in which the Tm value is between Tm −20 and Tm −27. The term "to hybridize" preferably relates to a hybridization under stringent hybridization conditions. Examples of such hybridizing DNA sequences which encode proteins with the immunoreactivity of HBeAg are DNA sequences of other HBV serotypes.

In a preferred embodiment of the recombinant yeast expression vectors according to the invention, the DNA sequence which is replicable in yeast is the 2μ or ars DNA sequence.

In another preferred embodiment of the recombinant yeast expression vectors according to the invention, the yeast promoter is the ADH-2, GAL or CYC1 promoter or a hybrid promoter composed thereof.

In another embodiment which is preferred according to the invention, the DNA sequence (c) is a DNA sequence which complements an amino-acid deficiency, preferably the LEU2 or URA3 gene.

The invention furthermore relates to yeasts which contain one of the recombinant yeast expression vectors according to the invention.

These yeasts preferably belong to the genus Schizosaccharomyces or Saccharomyces. Yeasts of the species Schizosaccharomyces pombe or Saccharomyces cerevisiae are particularly preferred.

In another embodiment the invention relates to processes for preparing a protein with the immunoreactivity of HBeAg, in which a yeast according to the invention, which contains a yeast expression vector according to the invention, is cultivated under suitable conditions and then the protein with the immunoreactivity of HBeAg is isolated from the culture.

The invention furthermore relates to proteins which have the immunoreactivity of HBeAg and can be obtained by the process according to the invention. This recombinant HBeAg prepared according to the invention in yeasts shows excellent HBeAg reactivity without HBcAg reactivity, without a denaturation step being necessary. This means that the proteins according to the invention with the immunoreactivity of HBeAg can be used for highly specific immunological assays or for immunization.

In another embodiment, the invention relates to a diagnostic reagent which contains a protein according to the invention with the immunoreactivity of HBeAg.

Moreover, the protein according to the invention with the immunoreactivity of HBeAg is, where appropriate, linked to a detectable label, preferably to a radioactive, enzymatic, fluorescent or chemiluminescent label. These labels are well known to those skilled in the art, for example iodine-125, horseradish peroxidase, β-galactosidase, fluorescein or acridinium ester.

In a preferred embodiment, the diagnostic reagent according to the invention is used for carrying out immunoassays for detecting HBeAg or anti-HBeAg antibodies. Examples of such immunoassays are the commercially obtainable assays already mentioned, as well as the assays mentioned in the examples.

The invention furthermore relates to medicinal agents which contain a protein according to the invention with the immunoreactivity of HBeAg, where appropriate in combination with a pharmaceutically tolerated excipient and/or diluent. These medicinal agents can, where appropriate, contain further immunogens such as HBsAg/HBcAg/preS, singly, in a mixture or as fusion protein. Thus the medicinal agents according to the invention contain HBeAg as vaccine alone; HBeAg as vaccine in a mixture with various other HBV antigens, such as HBsAg and/or HBcAg; HBeAg as vaccine with other HBV antigens as fusion protein; HBeAg as mixture with quite different vaccines (mixed vaccination or as enhancer of the response to vaccination); or HBeAg as fusion protein with a quite different protein (for example from HIV) for mixed vaccination or as enhancer of the immune response.

Finally, the invention relates to processes for the immunization of humans against HBV infections, in which a protein according to the invention with the immunoreactivity of HBeAg is inoculated, where appropriate in combination with a pharmaceutically tolerated excipient and/or diluent, in a conventional manner.

The medicinal agents according to the invention are preferably hepatitis vaccines.

The proteins according to the invention with the immunoreactivity of HBeAg can furthermore be used in a highly specific manner for the preparation of polyclonal or monoclonal anti-HBeAg-antibodies. This entails mammals, preferably rodents, such as rabbits, guinea-pigs, rats or mice, or else ungulates, such as sheep and horses, being immunized with the protein according to the invention, and then isolation of the antibodies from the blood serum. Monoclonal antibodies are prepared by the customary processes.

In order to be able to express HBeAg in yeasts, in a preferred embodiment a DNA sequence which carries the coding section from the codon for amino acid −29 in respect to the translational start codon of the HBcAg gene to the codon for amino acid +149 of the HBcAg gene was constructed. A DNA sequence which contains cleavage sites for some restriction endonucleases and has in position −3 upstream of the HBeAg translation start an adenin (A), so that efficient translation of the recombinant mRNA in yeasts is ensured, was attached at the 5' terminus. At the 3' terminus (which encodes amino acid +149) there follow two stop codons and a HindIII cloning site (FIG. 1). This DNA fragment was cloned into expression vectors for S. pombe and S. cerevisiae, and the recombinant plasmids were transformed into suitable strains which are now able to express HBeAg.

THE FIGURES SHOW

FIG. 1: Construction of expression vectors which encode the synthesis of HBeAg from Met −29 to Val +149 in Saccharomyces cerevisiae and Schizosaccharomyces pombe. The figure includes DNA sequences SEQ ID NO:4 and SEQ ID NO:5.

Figure 2:
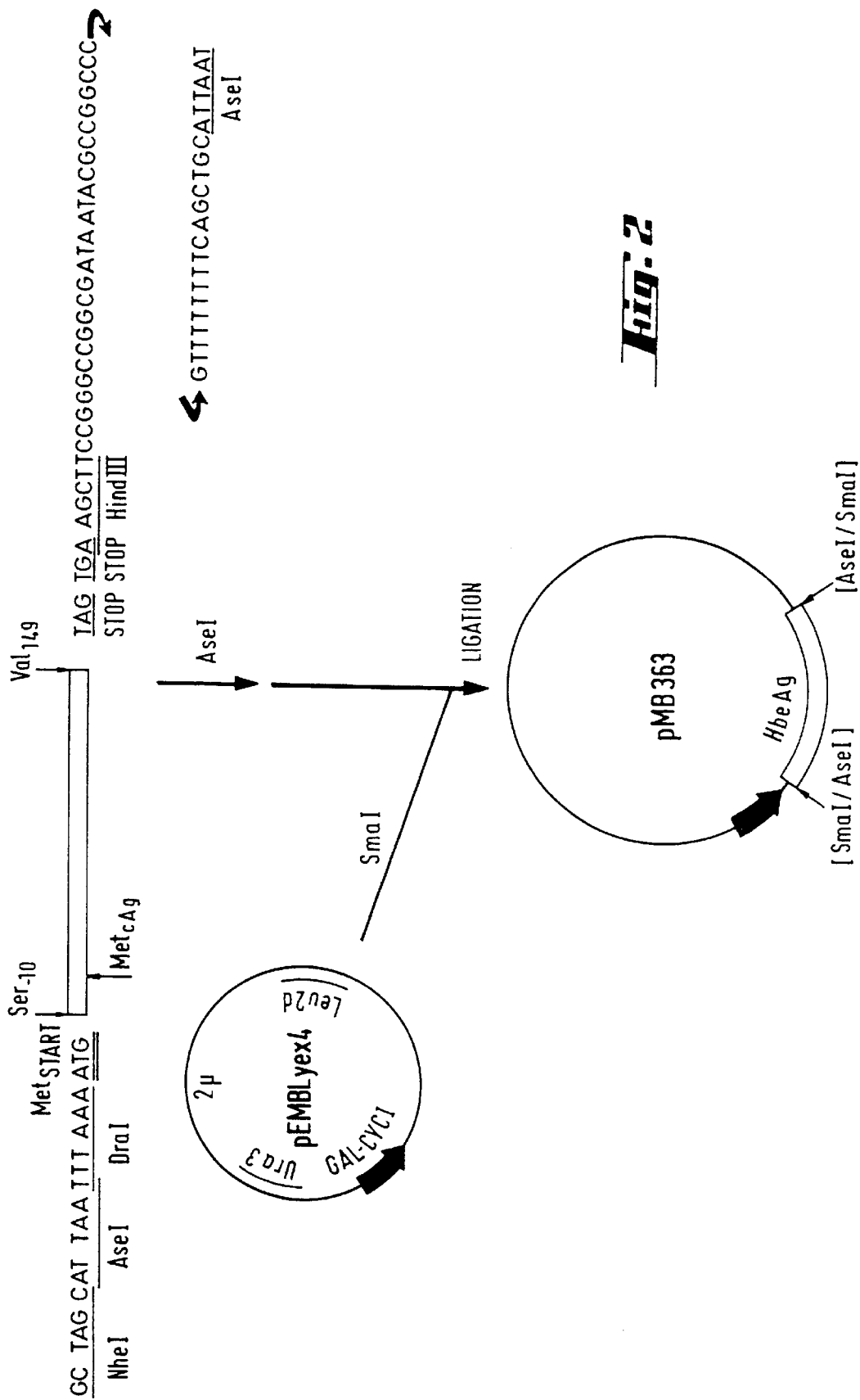

FIG. 2: Construction of an expression vector which encodes the synthesis of HBeAg from Ser −10 to Val +149 in Saccharomyces cerevisiae. The figure includes DNA sequences SEQ ID NO:6 and SEQ ID NO:7.

Figure 3:
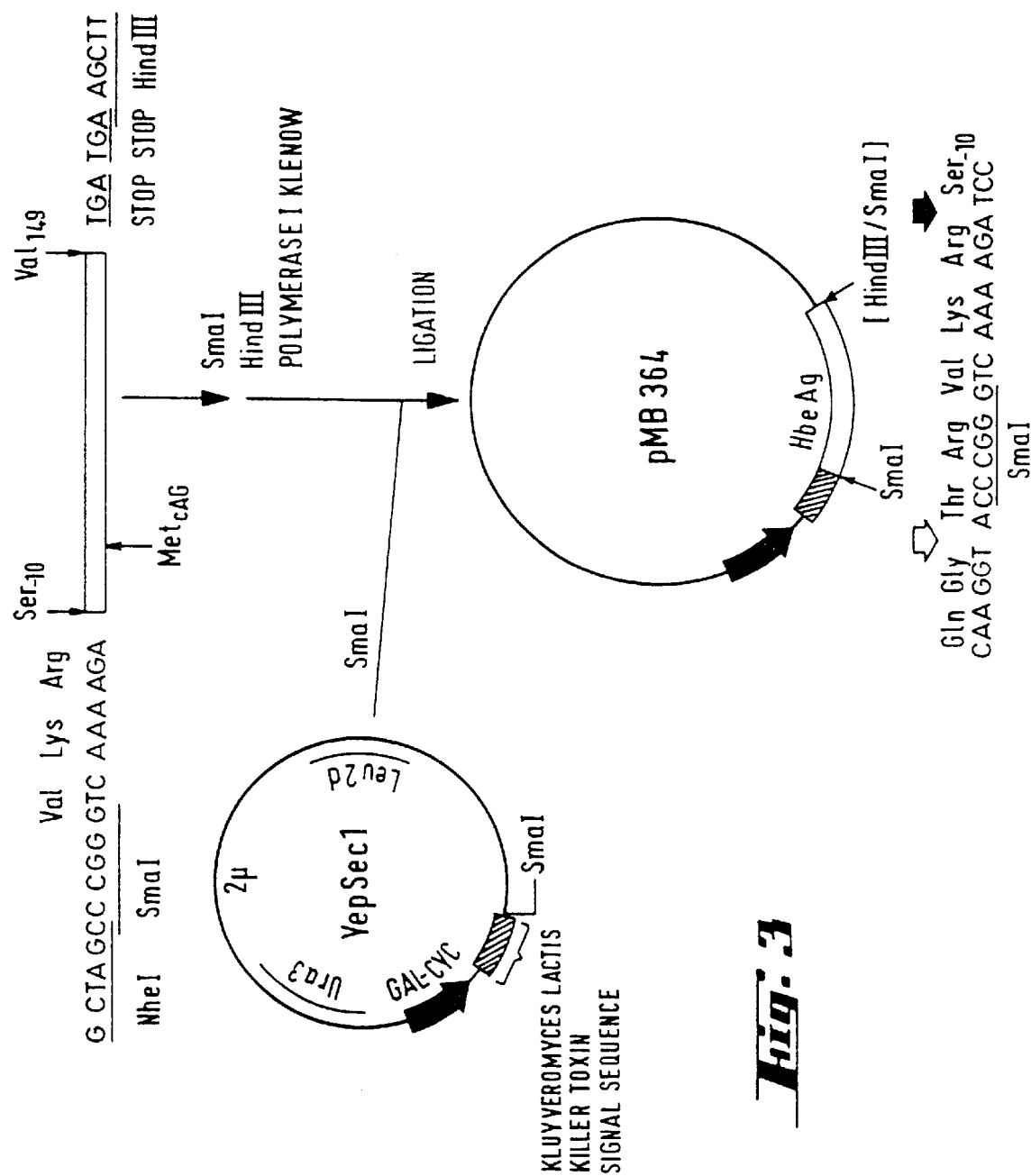

FIG. 3: Construction of an expression vector which encodes the synthesis of HBeAg from Ser −10 to Val +149 fused to a yeast signal sequence. The figure includes DNA sequences SEQ ID NO:8, SEQ ID NO:9 and SEQ ID NO:10.

The examples explain the invention. They describe, inter alia, the expression of HBeAg in the fission yeast Schizosaccharomyces pombe and in bakers' yeast Saccharomyces cerevisiae. Further information on the molecular biological methods used is described in Sambrook et al., "Molecular Cloning", 2nd Edition, Cold Spring Harbor, 1989.

EXAMPLE 1

Construction of a Vector for the Expression of HBeAg in S. pombe

The NheI/HindIII fragment which codes for HBeAg was treated with the Klenow fragment of polyreaseI (PolI) in the presence of nucleotides in order to repair the protruding single strands. The DNA fragment was ligated into the unique BamHI site of the S. pombe expression vector pMB332 (Broker and Bäuml, FEBS Lett. 248 (1989), 105–110) which had likewise been treated with PolI. Thus, the expression of HBeAg in the new plasmid pMB356 is under the control of the S. pombe ADH promoter. S. pombe ura4 strains can be complemented with this plasmid owing to the S. cerevisiae URA3 gene which is present on the vector-pMB356 and can be selected on minimal medium.

EXAMPLE 2

Construction of a Vector for the Expression of HBeAg in S. cerevisiae

The same HBeAg-encoding DNA fragment as in Example 1 was ligated into the unique SmaI site of the S. cerevisiae expression vector pEMBLyex4 (Cesareni and Murray "Genetic Engineering", Setlow, ed., Vol. 9 (1987), pages 135–153). The expression of HBeAg in the new plasmid pMB358 is thus under the control of the regulatable GAL-CYC1 hybrid promoter. S. cerevisiae ura3 and/or leu2 strains can be complemented with the vector pMB358 to uracil and leucine prototrophy respectively by the LEU2 and URA3 genes present on the vector.

EXAMPLE 3

Expression of HBeAg in Yeast

The plasmids pMB356 and 358 were transformed into S. pombe ura4 and S. cerevisiae respectively (for example strain C13ABYS86: leu2, ura3, his) by the LiCl method (Bröker, Biotechniques 5 (1987), 516–518), and transformants were selected on YNB medium.

Precultures with, in each case, 50 ml of YNB medium in 300 ml Erlenmeyer flasks were inoculated with single colonies and shaken at 30° C. for 48 h. Subsequently 10 ml of this preculture were transferred into 100 ml of YPD medium. The GAL-CYC1 promoter was induced by adding 2% galactose to the culture. The yield of HBeAg in S. cerevisiae can be considerably increased by growth conditions as described in German Patent 39 '651.

The cells were harvested after three to four days and disrupted with glass beads. The soluble supernatant contained immunoreactive HBeAg. The following buffer was preferably chosen for the cell disruption: 0.38% sodium citrate, pH 7.2; 0.85% NaCl with the addition of benzamidine chloride (2 mg/ml), phenylmethylsulfonyl fluoride (1 mM), polypren (1 mg/ml) and Antagosan (100 KIU/ml). The recombinant HBeAg can be stored in this buffer at −70° C. without loss of reactivity.

EXAMPLE 4

Construction of a Vector for the Expression of rHReAg Ser −10 to Val +149 in *S. cerevisiae*

Kim et al., loc. cit., have described how HBeAg synthesized in yeasts without the precore sequence and without the arginine-rich C terminus has no HBeAg reactivity but has HBcAg reactivity. An expression vector which, in contrast to the findings of Kim et al. ensures direct expression of "processed HBeAg" and provides a polypeptide without HBcAg reactivity was therefore developed.

In analogy to Example 2, a DNA fragment which codes for HBeAg from Ser −10 to Val +149 was cloned into the vector pEMBLyex4 (FIG. 2). Since this modified HBeAg DNA does not contain its own translation start codon in the plasmid pMB363, an ATG triplet was inserted upstream of the sequence to be translated so that the recombinant HBeAg starts with Met-Ser −10 at the amino terminus. This material is called rHBeAg Ser −10 to Val +149 hereinafter.

EXAMPLE 5

Construction of a Vector for the Expression of rBeAg Ss:: Ser −10 to Val +149 Fused to the Signal Sequence of the Killer Toxin of *Kluyveromyces lactis*

Kim et al., loc. cit., have postulated that HBeAg synthesized in yeasts must be translocated by a signal sequence in order to obtain HBeAg reactivity. They have undertaken for this purpose a fusion of the coding DNA sequence of HBeAg to the signal sequence of the *S. cerevisiae* α-factor.

It is shown hereinafter that fusion to the signal sequence of the *Kluyveromyces lactis* killer toxin is also possible.

HBeAg as encoded by the vector pMB363 (Example 4) ought not to be translocated but remain in the cytoplasm of the yeast cells. It ought to be possible, by fusing the HBeAg DNA to a signal sequence of a secretory yeast protein, possibly to secrete the recombinant HBeAg. The plasmid pMB364 was constructed for this purpose, as depicted in FIG. 3. Fusion to the signal sequence of the killer toxin of *K. lactis*, encoded by the vector YEpsec1 (Baldari et al., EMBO J. 6 (1987), 229–234) results in two possible specific cleavage sites; the postulated one of the killer toxin and five Amino acids further that of the alpha-factor of *Saccharomyces cerevisiae*. (Lys-Arg) One or both of these cleavage sites might be utilized, and the processed HBeAg secreted, at or during the translocation of the fusion protein.

No antigen with HBeAg activity was detectable in the culture broth from *S. cerevisiae* (pMB364), but it was in cell extracts of the recombinant yeasts. This material is called rHBeAg Ss:: Ser −10 to Val +149 hereinafter.

EXAMPLE 6

Specific Assays for HBeAg and HBcAg

The commercially available assay systems HBe (rDNA) (Abbott, Wiesbaden) and Enzygnost HBe (Behringwerke, Marburg) recognize not only HBeAg but also HBcAg, because the solid phases and conjugates used have been prepared using antibody preparations from HBV-infected people and thus contain anti-HBcAg-antibodies in addition to anti-HBeAg-antibodies. In order to be able to assay preparations containing HBeAg and/or HBcAg specifically for the particular antigen, specific immunoassays are necessary. We have therefore established a specific assay for the determination of HBcAg using a monoclonal antibody and an assay for the specific determination of HBeAg using monoclonal antibodies.

Immunoassay for HBcAg

100 μl of the particular sample are incubated in the wells, coated with a monoclonal anti-HBcAg antibody, of a microtiter plate at 37° C. for 1 h. This is followed by washing twice and then incubating with a monoclonal anti-HBcAg/POD conjugate (M. Noah, H.-P. Harthus, Bio Engineering 4 (1988), 22–30; Salfeld et al., J. Virol. 63 (1989), 798–808) at 37° C. for 1 h. A renewed washing step is followed by addition of 100 μl of chromogen/substrate solution (tetramethylbenzidine, see Enzygnost HIV 1+2, Behringwerke, Marburg). The chromogen reaction is stopped after 30 minutes by adding 100 μl of 0.5 N $H_2SO_4$.

The extinction is measured at a wavelength of 450 nm. All samples whose extinction is more than 0.05 E above the mean of the negative controls are regarded as HBcAg-positive.

Immunoassay for HBeAg (Monoclonal)

The immunoassay for HBeAg follows the same scheme as the assay for HBcAg; the only difference is the use of microtiter plates which are coated with monoclonal anti-HBeAg-antibodies and of a conjugate of monoclonal anti-HBeAg-antibodies. The production of monoclonal anti-HBeAg-antibodies has been described in the literature several times (M. Imai et al., J. of Immunol. 128 (1982), 69–75; R. B. Ferns, R. S. Tedder, J. Gen. Virol. 65 (1984), 899–908). The commercial HBeAg assay supplied by Sorin also now uses monoclonal antibodies. Samples whose extinction is more than 0.05 E above the mean of the negative controls are regarded as HBeAg-positive.

EXAMPLE 7

Sensitivity and Specificity of the Enzygnost HBe, of the Monoclonal HBeAg and of the Monoclonal HBcAg ELISAs Various materials were employed in the Enzygnost HBe, HBeAg monoclonal and HBcAg monoclonal assay systems in order to show the sensitivity and specificity of the assays and to demonstrate the HBeAg and/or HBcAg reactivity of these materials. These materials comprised a recombinant material from *E. coli*, which comprised the amino acids of the C-sequence up to +183 (r183/Biogen, Cambridge, Mass., USA) and the same material after SDS treatment (r183 SDS) in order to reduce the HBcAG reactivity and to induce or to increase the HBeAg reactivity (R. B. Ferns, R. S. Tedder, loc. cit.).

Also used was a truncated recombinant material from *E. coli*, which corresponded to only the amino acids of the C-sequence up to +144 (r144, Biogen), and native HBeAg from human serum, the content of which was calibrated using standard material from the Paul-Ehrlich Institute. Since HBeAg-containing human sera always contain anti-HBcAg antibodies, this material is outstandingly suitable for comparing the analytical sensitivity of two assay systems with regard to HBeAg reactivity when one assay recognizes HBcAg in addition to HBeAg. This material is unsuitable for use in an assay for HBcAg because the anti-HBcAg antibodies would completely mask any HBcAg reactivity present. However, for the sake of completeness, these data are also given in Table 1.

In particular, when the results of the Enzygnost HBe are compared with the HBeAg monoclonal assay, the higher sensitivity for HBeAg in the monoclonal assay is evident in Table 1A.

By contrast, with r183 the Enzygnost HBe appears to be about 20× more sensitive, which is attributable to the content of HBcAg and HBeAg reactivity in this material and to the additional specificity of the Enzygnost HBe for HBcAg too.

If the recombinant material r183 is now compared in the HBcAg monoclonal and in the HBeAg monoclonal it is evident that this material has HBcAg reactivity which is at least 7 times more pronounced than the HBeAg reactivity (Table 1B). The SDS treatment reduces the HBcAg reactivity to less than 1/100 but the HBeAg reactivity to only about 1/5. This means that the HBcAg reactivity is still about 1/300 of the HBeAg reactivity (Table 1B and 1C).

The recombinant material r144 exhibits about 1/6 of the HBeAg reactivity as HBcAg reactivity (Table 1D).

By contrast, the recombinant yeast material according to the invention (Example 3) displays without further treatment as HBcAg reactivity less than 1/3000 of the HBeAg reactivity (Table 1E); see Example 9 for further estimation of the HBcAg cross-reactivity of this material.

In summary, Table 1 shows that
a) Enzygnost[R] HBe is able to recognize both HBeAg and HBcAg;
b) Enzygnost[R] HBe monoclonal is specific for HBeAg and more than twice as sensitive as Enzygnost[R] HBe;
c) the HBc monoclonal assay is specific for HBcAg;
d) r183 displays both HBeAg and HBcAg reactivity and loses to some extent HBcAg and HBeAg reactivity by SDS treatment:
e) r144 displays both HBeAg and markedly HBcAg reactivity;
f) the recombinant yeast HBeAg according to the invention with an HBcAg activity of less/than 1/3000 of the HBeAg reactivity is virtually free of HBcAg reactivity. These low cross-reactivities (1:10000) might have been caused by the monoclonal anti-HBcAg antibody.

TABLE 1

Comparison of the sensitivity and specificity of the Enzygnost HBe, of the monoclonal HBeAg and of the monoclonal HBcAg assays

| Sample | | E. HBe [mE] | HBeAg monocl. [mE] | HBcAg monocl. [mE] |
|---|---|---|---|---|
| neg. control | | 19 | 3 | 5 |
| HBeAg serum A | 7.5 U/ml | 810 | <2,500 | 6 |
| | 3.75 U/ml | 613 | 1,725 | 8 |
| | 1.88 U/ml | 335 | 850 | 5 |
| | 0.94 U/ml | 179 | 522 | 6 |
| | 0.47 U/ml | 96 | 248 | 6 |
| | 0.23 U/ml | 75 | 125 | 6 |
| | 0.12 U/ml | 46 | 56 | 5 |
| analytical sensitivity | | 0.24 E/ml | 0.11 E/ml | — |
| r183 | 10 µg/ml | >2,500 | >2,500 | >2,500 |

TABLE 1-continued

Comparison of the sensitivity and specificity of the Enzygnost HBe, of the monoclonal HBeAg and of the monoclonal HBcAg assays

| Sample | | E. HBe [mE] | HBeAg monocl. [mE] | HBcAg monocl. [mE] |
|---|---|---|---|---|
| B | 1 µg/ml | >2,500 | >2,500 | >2,500 |
| | 100 ng/ml | >2,500 | 366 | >2,500 |
| | 10 ng/ml | 665 | 11 | 39 |
| | 1 ng/ml | 35 | 5 | 5 |
| r183 SDS | 10 µg/ml | >2,500 | >2,500 | 232 |
| C | 1 µg/ml | 455 | 1,040 | 5 |
| | 100 ng/ml | 54 | 79 | 3 |
| | 10 ng/ml | 25 | 7 | 4 |
| | 1 ng/ml | 20 | 3 | 6 |
| r144 | 1:100 | >2,500 | >2,500 | >2,500 |
| D | 1:1,000 | >2,500 | >2,500 | >2,500 |
| | 1:10,000 | >2,500 | >2,500 | >2,500 |
| | 1:100,000 | >2,500 | >2,500 | >2,500 |
| | 1:1,000,000 | >2,500 | >2,500 | 1,039 |
| | 1:10,000,000 | 1,020 | 1,829 | 8 |
| | 1:100,000,000 | 193 | 364 | 13 |
| | 1:1,000,000,000 | 77 | 122 | 5 |
| Yeast rHBeAg SC 358-3004 | | | | |
| undiluted | | <2,500 | <2,500 | 6 |
| E | 1:10 | 1.263 | <2,500 | 8 |
| | 1:100 | 15.1 | 439 | 5 |
| | 1:1,000 | 32 | 28 | 6 |
| | 1:10,000 | 23 | n.d. | 4 |

EXAMPLE 8

Immunoreactivity of the from S. pombe

The HBeAg-containing soluble cell extracts of individual transformations of S. pombe according to Example 3 were assayed for HBeAg and HBcAg reactivity in the various immunoassays. Four individual transformations (A–D) were cultured in YNB medium, and the soluble cell extract was investigated.

As is evident from Table 2, the clones YNB A, YNB B, YNB C and YNB D display good HBeAg reactivity without even just a hint of HBcAg reactivity.

TABLE 2

Immunoreactivity of the HBeAg from S. pombe

| Sample | Enz. HBe [mE] | HBeAg monocl. [mE] | HBcAg monocl. [mE] |
|---|---|---|---|
| neg. control | 25 | 17 | 17 |
| Clone YNB A | | | |
| undiluted | 225 | 606 | 11 |
| 1:10 | 29 | 60 | 8 |
| Clone YNB B | | | |
| undiluted | 141 | 451 | 14 |
| 1:10 | 31 | 40 | 8 |
| Clone YNB C | | | |
| undiluted | 938 | 1924 | 11 |
| 1:10 | 71 | 22.6 | 11 |
| Clone YNB D | | | |
| undiluted | 580 | 1263 | 15 |
| 1:10 | 98 | 298 | 9 |

EXAMPLE 9

Immunoreactivity of the HBeAg from S. cerevisiae

The HBeAg-containing soluble cell extracts of individual transformations of S. cerevisiae according to Example 3 were assayed for HBeAg and HBcAg reactivity in various immunoassays.

5 individual transformations (SC-A to SC-E) were cultured, and the soluble cell extract was investigated.

The supernatants showed a very high HBeAg reactivity, with the HBcAg reactivity amounting to only about 1:10,000 of the HBeAg reactivity.

TABLE 3

Immunoreactivity of the HBeAg from *S. cerevisiae*

| Sample | | Enz. HBe [mE] | HBeAg monocl. [mE] | HBcAg monocl. [mE] |
|---|---|---|---|---|
| neg. control | | 22 | 9 | 15 |
| rHBcAg 100 ng/ml | | >2,500 | 770 | >2,500 |
| SC-A | undiluted | >2,500 | >2,500 | 34 |
| | 1:10 | >2,500 | >2,500 | 19 |
| | 1:100 | n.d. | >2,500 | n.d. |
| | 1:1,000 | n.d. | 761 | n.d. |
| | 1:10,000 | n.d. | 51 | n.d. |
| SC-B | undiluted | >2,500 | >2,500 | 35 |
| | 1:10 | >2,500 | >2,500 | 15 |
| | 1:100 | n.d. | >2,500 | n.d. |
| | 1:1,000 | n.d. | 297 | n.d. |
| | 1:10,000 | n.d. | 23 | n.d. |
| SC-C | undiluted | >2,500 | >2,500 | 67 |
| | 1:10 | >2,500 | >2,500 | 21 |
| | 1:100 | n.d. | >2,500 | n.d. |
| | 1:1,000 | n.d. | 626 | n.d. |
| | 1:10,000 | n.d. | 57 | n.d. |
| SC-D | undiluted | >2,500 | >2,500 | 32 |
| | 1:10 | >2,500 | >2,500 | 17 |
| | 1:100 | n.d. | >2,500 | n.d. |
| | 1:1,000 | n.d. | 585 | n.d. |
| | 1:10,000 | n.d. | 48 | n.d. |
| SC-E | undiluted | >2,500 | >2,500 | 32 |
| | 1:10 | >2,500 | >2,500 | 17 |
| | 1:100 | n.d. | >2,500 | n.d. |
| | 1:1,000 | n.d. | 519 | n.d. |
| | 1:10,000 | n.d. | 44 | n.d. |

EXAMPLE 10

Immunoassay for the Determination of anti-HBeAg-antibodies From Human Samples Using a Conventional Neutralization Reagent and a Neutralization Reagent From Recombinant HBeAg From S.c.

(A) Using an assay with polyclonal human solid-phase and conjugate antibodies

The Enzygnost HBe uses antibody preparations from human sera as solid-phase and conjugate antibodies. Likewise, the material used as HBeAg is derived from the blood of infected people. In order to ensure that the recombinant HBeAg is just as suitable as the HBeAg from blood for the determination of anti-HBeAg-antibodies from human samples, the assay was carried out on the one hand as specified in the package insert and on the other hand with an appropriate dilution of the recombinant material from Example 3.

Used as samples was material from people who had an acute or chronic infection and also displayed other parameters of a hepatitis B virus infection. In addition, in order to determine the analytical sensitivity, an anti-HBeAg-material which was calibrated using standard material from the Paul-Ehrlich Institute, Frankfurt, was employed.

As Tables 4a) and b) show, the results with the recombinant HBeAg are absolutely comparable with the results of the conventional material.

TABLE 4A

Comparison of the Enzygnost HBe with conventionally obtained HBeAg and with recombinant HBeAg as neutralization reagent
Analytical sensitivity based on a secondary standard calibrated using standard material from the Paul-Ehrlich Institute, Frankfurt

| | Enzygnost HBe | |
|---|---|---|
| Sample | conv. HBeAg [mE] | rec. HBeAg [mE] |
| neg. control | 603 | 1,094 |
| cut off | 302 | 547 |
| 0.75 E/ml | 252 | 84 |
| 0.38 E/ml | 435 | 155 |
| 0.19 E/ml | 519 | 323 |
| 0.09 E/ml | 589 | 469 |
| 0.05 E/ml | 620 | 657 |
| 0.02 E/ml | 574 | 787 |
| analyt. sensitivity | 0.65 U/ml | 0.08 U/ml |

TABLE 4B

Comparison of the Enzygnost HBe with conventionally obtained HBeAg and with recombinant HBeAg as neutralization reagent in the anti-HBe-positive panel

| | Enzygnost HBe | |
|---|---|---|
| Sample | conv. HBeAg [mE] | rec. HBeAg [mE] |
| neg. control | 1,276 | 1,727 |
| pos. control | 43 | 59 |
| cut off | 638 | 864 |
| No. KK 2 | 57 | 43 |
| 3 | 70 | 26 |
| 4 | 23 | 2.6 |
| 5 | 25 | 30 |
| 7 | 34 | 25 |
| 8 | 22 | 30 |
| 12 | 516 | 88 |
| 15 | 31 | 61 |
| 16 | 247 | 101 |
| 21 | 48 | 52 |
| 22 | 28 | 50 |
| 23 | 48 | 40 |
| 24 | 80 | 30 |
| 25 | 53 | 47 |
| 30 | 75 | 67 |
| 35 | 65 | 45 |
| 36 | 33 | 59 |
| 37 | 158 | 48 |
| 38 | 107 | 40 |
| 40 | 51 | 39 |
| 41 | 56 | 48 |
| 42 | 74 | 35 |
| 44 | 90 | 36 |
| 46 | 32 | 29 |
| 50 | 220 | 129 |

(B) Using am assay with monoclonal solid-phase and conjugate antibodies

The monoclonal assay for HBeAg described in Example 6 was modified by the use of a conventional neutralization reagent or of a neutralization reagent with recombinant HBeAg in such a way that it was possible to detect anti-HBeAg antibodies from human samples. The same material as in 10A was used as samples. As Tables 5 a) and b) show, the results of the conventional and of the recombinant material are absolutely comparable in the monoclonal assay too.

TABLE 5

Comparison of the HBe monoclonal with conventionally obtained HBeAg and recombinant HBeAg as neutralization reagent

| Sample | Enzygnost HBe | |
|---|---|---|
| | conv. HBeAg [mE] | rec. HBeAg [mE] |
| 5 a) Analytical sensitivity based on a secondary standard calibrated using standard material from the Paul-Ehrlich Institute, Frankfurt | | |
| Control | 1,508 | 1,513 |
| cut off | 754 | 757 |
| 0.75 E/ml | 142 | 112 |
| 0.38 E/ml | 375 | 279 |
| 0.19 E/ml | 723 | 549 |
| 0.09 E/ml | 985 | 769 |
| 0.05 E/ml | 1,265 | 1,022 |
| 0.02 E/ml | 1,501 | 1,207 |
| analyt. sensitivity | 0.18 E/ml | 0.11 E/ml |
| 5 b) In the anti-HBe-positive panel | | |
| neg. control | 1,806 | 1,381 |
| pos. control | 6 | 12 |
| cut. off | 903 | 690 |
| No. KK 2 | 6 | 10 |
| 3 | 8 | 3 |
| 4 | 4 | 4 |
| 5 | 3 | 13 |
| 7 | 3 | 4 |
| 8 | 3 | 31 |
| 12 | 1.74 | 168 |
| 15 | 3 | 7 |
| 16 | 114 | 184 |
| 21 | 5 | 18 |
| 22 | 3 | 14 |
| 23 | 3 | 6 |
| 24 | 5 | 3 |
| 25 | 3 | 4 |
| 30 | 3 | 14 |
| 35 | 5 | 8 |
| 36 | 3 | 5 |
| 37 | 45 | 45 |
| 38 | 23 | 49 |
| 40 | 11 | 4 |
| 41 | 19 | 21 |
| 42 | 30 | 6 |
| 44 | 122 | 19 |
| 46 | 4 | 4 |
| 50 | 130 | 112 |

EXAMPLE 11

Immunoreactivity of the Recombinant HBeAg Ser −10 to Val +149 With and Without Upstream Signal Sequence From *K. lactis*

Table 6 shows that the materials from Example 4 (rHBeAg Ser −10 to Val +149) and from Example 5 (rHBeAg Ss:: Ser −10 to Val +149) also have good HBeAg reactivity and display no HBcAg reactivity.

TABLE 6

Immunoreactivity of recombinant HBeAg Ser −10 to Val +149 and HBeAg Ss:: Ser −10 to Val +149

| Sample | Enz. HBe [mE] | HBeAg monocl. [mE] | HBcAg monocl. [mE] |
|---|---|---|---|
| neg. control | 18 | 8 | 6 |
| rHBeAg Ser −10 to Val +149 | | | |
| 1:10 | 1,780 | >2,500 | 7 |
| 1:100 | 185 | 1,755 | 6 |
| 1:1,000 | 43 | 188 | 5 |
| 1:10,000 | 20 | 29 | 6 |
| rHBeAg Ss:: Ser −10 to Val +149 | | | |
| 1:10 | >2,500 | >2,500 | 8 |
| 1:100 | 1,098 | >2,500 | 7 |
| 1:1,000 | 118 | 1,077 | 7 |
| 1:10,000 | 35 | 147 | 6 |

---

What is claimed:

1. A recombinant yeast expression vector comprising a DNA sequence encoding a protein with the immunoreactivity of Hepatitis B Virus E Antigen (HBeAg), and not the immunoreactivity of Hepatitis B Virus C Antigen (HBcAg), wherein the DNA sequence starts at amino acid position −29 of the precore (pre-C) sequence and stops at amino acid position +149 of the C sequence.

2. The recombinant yeast expression vector as claimed in claim 1, which further comprises:

(a) a DNA sequence which is replicable in yeast;

(b) a yeast promoter;

(c) a transcription stop signal; and (d) a DNA sequence which encodes a yeast selection marker, wherein the recombinant yeast expression vector, the DNA sequence which is replicable in yeast, the yeast promoter, the transcription stop signal, and the DNA sequence which encodes a yeast selection marker are operatively linked.

3. The recombinant yeast expression vector as claimed in claim 2, wherein the DNA sequence which is replicable in yeast is the 2$\mu$ yeast origin of replication.

4. The recombinant yeast expression vector as claimed in claim 2, wherein the yeast promoter is ADH−2 promoter, GAL promoter, CYC1 promoter, or a hybrid promoter composed of GAL and CYC1 promoter elements.

5. The recombinant yeast expression vector as claimed in claim 2, wherein the DNA sequence (d) complements an amino acid deficiency, wherein said amino acid deficiency is a yeast selection marker.

6. The recombinant yeast expression vector as claimed in claim 5, wherein the DNA sequence (d) is the LEU2 gene.

7. A yeast which contains a recombinant yeast expression vector comprising a DNA sequence encoding a protein with the immunoreactivity of Hepatitis B Virus E Antigen (HBeAg), and not the immunoreactivity of Hepatitis Virus C Antigen (HBcAg), wherein the DNA sequence starts at amino acid position −29 of the precore (pre-C) sequence and stops at amino acid position +149 of the C sequence.

8. The yeast as claimed in claim 7, which belongs to the genus Schizosaccharomyces or Saccharomyces.

9. The yeast as claimed in claim 8, which belong to the species Schizosaccharomyces pombe or Saccharomyces cerevisiae.

10. A process for the preparation of a protein with the immunoreactivity of HBeAg and without any reactivity of HBcAg, comprising the steps of:

incorporating into a yeast cell a recombinant yeast expression vector comprising a DNA sequence which encodes a protein with the immunoreactivity of HBeAg, wherein the DNA sequence starts at amino acid position −29 of the pre-C sequence and stops at amino acid position +149 of the C sequence;

culturing the yeast cell under suitable conditions; and isolating from the culture the protein with the immunoreactivity of HBeAg.

11. The recombinant yeast expression vector as claimed in claim 2, wherein the DNA sequence (d) is the URA3 gene.

12. A process for the preparation of a protein with the immunoreactivity of HBeAg and without any reactivity of HBcAg, comprising the steps of:

incorporating into a yeast cell a recombinant yeast expression vector comprising:

(a) a DNA sequence which encodes a protein with the immunoreactivity of HBeAg, wherein the DNA sequence starts at amino acid position −29 of the pre-C sequence and stops at amino acid position +149 of the C sequence;

(b) a DNA sequence which is replicable in yeast;

(c) a yeast promoter;

(d) a transcription stop signal; and (e) a DNA sequence which encodes a yeast selection marker, wherein the recombinant yeast expression vector, the DNA sequence which is replicable in yeast, the yeast promoter, the transcription stop signal, and the DNA sequence which encodes a yeast selection marker are operatively linked;

culturing the yeast cell under suitable conditions; and isolating from the culture the protein with the immunoreactivity of HBeAg.

* * * * *